(12) United States Patent
Burke

(10) Patent No.: US 9,808,437 B2
(45) Date of Patent: Nov. 7, 2017

(54) MONOUNSATURATED FATTY ACID COMPOSITIONS AND USE FOR TREATING ATHEROSCLEROSIS

(71) Applicant: BURKE & BOYER NYC, New York, NY (US)

(72) Inventor: John M. Burke, Concord Township, OH (US)

(73) Assignee: BURKE & BOYER NYC, New York, NY (US)

(*) Notice: Subject to any disclaimer, the term of this patent is extended or adjusted under 35 U.S.C. 154(b) by 0 days.

(21) Appl. No.: 15/113,739

(22) PCT Filed: Oct. 14, 2015

(86) PCT No.: PCT/US2015/055504
§ 371 (c)(1),
(2) Date: Jul. 22, 2016

(87) PCT Pub. No.: WO2016/061207
PCT Pub. Date: Apr. 21, 2016

(65) Prior Publication Data
US 2017/0216237 A1  Aug. 3, 2017

Related U.S. Application Data

(60) Provisional application No. 62/064,207, filed on Oct. 15, 2014.

(51) Int. Cl.
*A61K 31/201* (2006.01)
(52) U.S. Cl.
CPC .................................. *A61K 31/201* (2013.01)
(58) Field of Classification Search
None
See application file for complete search history.

(56) References Cited

U.S. PATENT DOCUMENTS

| 6,391,369 B1 | 5/2002 | Kincs et al. |
| 8,703,818 B2 | 4/2014 | Green |
| 2009/0311367 A1 | 12/2009 | Perry |
| 2009/0312297 A1 | 12/2009 | Hotamisligil et al. |
| 2014/0364416 A1 | 12/2014 | Green |
| 2015/0224073 A1 | 8/2015 | Green |

FOREIGN PATENT DOCUMENTS

WO    2013007700 A1    1/2013

OTHER PUBLICATIONS

Non-Final Office Action dated Aug. 12, 2015 for U.S. Appl. No. 14/242,460, filed Apr. 1, 2014.
Non-Final Office Action dated Jul. 30, 2015 for U.S. Appl. No. 14/635,722, filed Mar. 2, 2015.
Search Report and Written Opinion of PCT/US2015/055504 dated Jan. 11, 2016.

*Primary Examiner* — Brian J Davis
(74) *Attorney, Agent, or Firm* — Silvia Salvadori, P.C.; Silvia Salvadori

(57) ABSTRACT

Compositions comprising high concentration of monounsaturated fatty acids having low melting points and high iodine values and use of such compositions as dietary supplements, nutraceuticals or pharmaceuticals for reducing atherosclerotic plaque in mammals. It has been found that high concentrations of monounsaturated fatty acids (MUFAs) having low melting point temperatures and iodine values of about 50 to about 130 can be used to effectively treat atherosclerosis. Epidemiological studies suggest that those populations consuming large quantities of C18:1 found in olive oil are protected against vascular diseases such as atherosclerosis.

23 Claims, 2 Drawing Sheets

MONOUNSATURATED FATTY ACID COMPOSITIONS AND USE FOR TREATING ATHEROSCLEROSIS

This application is a U.S. national stage of PCT/US2015/055504 filed on 14 Oct. 2015, which claims priority to and the benefit of U.S. Provisional Application No. 62/064,207, filed on 15 Oct. 2014, the contents of which are incorporated herein by reference in their entireties.

FIELD OF INVENTION

The present invention relates to high concentrations of monounsaturated fatty acids compositions having low melting points and high iodine values for treating atherosclerotic plaques.

BACKGROUND OF INVENTION

Atherosclerosis and its associated vascular complications are the principal cause of cardiovascular and cerebrovascular diseases leading to heart attacks and strokes. Atherosclerosis is a disease characterized by deposits of fatty material or plaques on the inner walls of the arteries. Over time the plaque deposits increase in size blocking oxygen from reaching the downstream organs. When vital arteries to the heart are blocked, it can cause angina and heart attack and possibly leading to death. Atherosclerosis also affects the arteries leading to the brain causing cerebral thrombosis or a stroke which can result in muscular paralysis, loss of cognitive capacity and the risk of dementia. Arteries in the leg may also become blocked with atherosclerotic plaque causing pain and difficulty in walking and possibly the risk of necrosis and gangrene of the effected tissue.

Atherosclerotic plaque is theorized to be caused by the interaction of monocytes migrating across the arterial wall in response to accumulation of oxidized cholesterol. Inside the arterial wall, the monocytes engorge themselves on the oxidized cholesterol and are converted into fat-laden "foam cells." When the foam cells die, they release their lipid content, creating a lipid core inside the arterial wall. The buildup of the lipid core along with calcium, fatty acids and other materials eventually form plaque. Over time the plaque calcifies and hardens. Continued plaque growth within the arterial wall causes the arterial wall to expand outward to avoid encroaching into the lumen. When the plaque growth reaches beyond the capacity of the arterial wall to compensate, the plaque intrudes into the lumen. Rupturing of the plaque exposes the lipid core to the blood creating blood clots. The clots can block the artery cutting off blood flow or detach and obstruct an artery downstream. Patients suffering from atherosclerosis may be asymptomatic for many years while the atherosclerotic plaque builds up in the arterial walls. Most often patients are unaware of the disease until a stroke or heart attack occurs.

Most methods for treating atherosclerosis involve uses of prescription medication. For instance, the group of medications known as statins are prescribed for treating atherosclerosis in patients with high cholesterol but its effects in women and people over the age of 70 are unclear. Niacin, a vitamin, has also been prescribed for treating atherosclerosis but it causes flushing of the skin and increases blood sugar levels which can be risky for diabetic patients. Drugs for limiting the absorption of cholesterol like Ezetimibe have also been prescribed for patients with atherosclerosis but its efficacy in reducing the risk of heart attacks and strokes in those patients is unclear.

Other methods for treating atherosclerosis include medical procedures such as surgical stenting, surgical excision of the plaque, ablation of the plaque, and bypass surgery/grafting. These procedures are costly and not without risks and limitations. Stenting of the arterial wall comes with the risks of blood clots and the stent itself can become blocked over time. Surgical excision and ablation can release plaque particles that can lead to obstruction of arteries leading to the brain causing a stroke. Grafting the arteries with autologous blood vessels can also lead to other complications such as stroke, heart attacks, reduced kidney function and irregular heartbeats. All these surgical procedures are also severely limited by targeting only specific arteries and leaving other arteries that may be affected by atherosclerosis untreated.

Atherosclerosis can be prevented or mitigated by modification of risk factors such as smoking cessation, increase exercise, managing weight in obese patients, lowering blood pressure, monitoring blood lipid levels and changing poor dietary habits. Additionally, patients at risk of developing atherosclerosis are advised to reduce their cholesterol and saturated fat intake by substituting their diets with unsaturated fatty acids found in natural oils such as olive oil. Olive oil and other naturally occurring oils, however, also contain other undesirable fatty acids that has been known to contribute to atherosclerosis.

Despite the advances in the study, prevention, and treatment of atherosclerosis, it remains a leading cause of death or disability in people. Accordingly, there exists a need for effective treatment of atherosclerotic plaques without the need for invasive medical procedures and risky side effects from prescription pharmaceuticals.

SUMMARY OF INVENTION

It has been found that high concentrations of monounsaturated fatty acids (MUFAs) having low melting point temperatures and iodine values of about 50 to about 130 can be used to effectively treat atherosclerosis. Epidemiological studies suggest that those populations consuming large quantities of C18:1 found in olive oil are protected against vascular diseases such as atherosclerosis. Natural oils such as olive oils, however, also contain high concentrations of other saturated fatty acids that may contribute to plaque formation and polyunsaturated fatty acids that may undergo cross-linking reactions to produce unwanted covalently bound complexes. It has been discovered that administering compositions comprising high concentrations of MUFAs having low melting points of about 29° C. to about 34° C. and high iodine values of about 50 to about 130 significantly reduces atherosclerotic lesions in vascular tissues. The MUFAs contemplated herein are blends or mixtures of fatty acids having a short acyl length chain and long acyl length chain. Administration of said compositions as dietary supplements, nutraceuticals, and pharmaceuticals has the added benefit of treating atherosclerosis without the risks and cost of surgical procedures.

In one embodiment of the invention, MUFA compositions are provided comprising at least two fatty acids groups having a melting point of about 29° C. to about 34° C. and an iodine value of about 50 to about 130 wherein the first MUFA group has an acyl carbon length chain of 16 carbons or less ("short carbon chain group") and the second MUFA group has an acyl carbon length chain of 18 carbons or more ("long carbon chain group") and the total weight concentration of the first and second fatty acid group is greater than about 80% by weight of the composition.

In another embodiment of the invention, at least one member of MUFA in the first group is selected from C12:1, C14:1 and C16:1 fatty acids and at least one member of MUFA in the second group is selected from C22:1, C20:1 and C18:1 fatty acids.

In another embodiment of the invention, a first group comprises short carbon chain MUFAs present at about 18% to about 40% by weight of the composition and a second MUFA group comprises long carbon chain MUFAs present at about 40% to about 80% by weight of the composition wherein the total concentration of the MUFAs in the composition is greater than 80%.

In another embodiment of the invention, a first group comprises short carbon chain MUFAs present at about 20% to about 40% by weight of the composition and a second MUFA group comprises long carbon chain MUFAs present at about 60% to about 80% by weight of the composition wherein the total concentration of the MUFAs in the composition is greater than 80%.

In another embodiment of the invention, a first group comprises short carbon chain MUFAs present at about 18% to about 23% by weight of the composition and a second MUFA group comprises long carbon chain MUFAs present at about 60% to about 80% by weight of the composition wherein the total concentration of the MUFAs in the composition is greater than 80%.

In another embodiment of the invention, a first group comprises short carbon chain MUFAs present at about 20% to about 23% by weight of the composition and a second MUFA group comprises long carbon chain MUFAs present at about 60% to about 80% by weight of the composition wherein the total concentration of the MUFAs in the composition is greater than 80%.

In another embodiment of the invention, high concentration compositions of short and long carbon chain MUFAs are provided that further comprises up to about 15% by weight of saturated and polyunsaturated fatty acids.

In another embodiment of the invention, compositions are provided for treating atherosclerosis with high concentrations of MUFAs comprising about 18% to about 40%, and preferably about 20% to about 40%, and more preferably about 18% to about 23%, and even more preferably about 20% to about 23% by weight of C16:1 fatty acid. Said composition also comprises about 40% to about 80% and preferably about 60% to about 80% by weight of C18:1 fatty acid wherein the total concentration of C16:1 and C18:1 is greater than 80% by weight of the composition. The C16:1 and C18:1 MUFA compositions may optionally include up to 15% saturated and polyunsaturated fatty acids.

In another embodiment of the invention, methods are provided for treating atherosclerosis with high concentrations of MUFAs comprising compositions of about 18% to about 40%, preferably about 20% to about 40%, more preferably about 18% to about 23%, and even more preferably about 20% to about 23% by weight of short carbon chain MUFAs and about 40% to about 80% and more preferably about 60% to about 80% by weight of long carbon chain MUFAs wherein the total concentration of said MUFAs is greater than 80% by weight of the composition. Treatment comprises administering said MUFA compositions daily at about 15 grams per 40 kg of body weight for at least 8 weeks.

DETAILED DESCRIPTION

Figure 1:
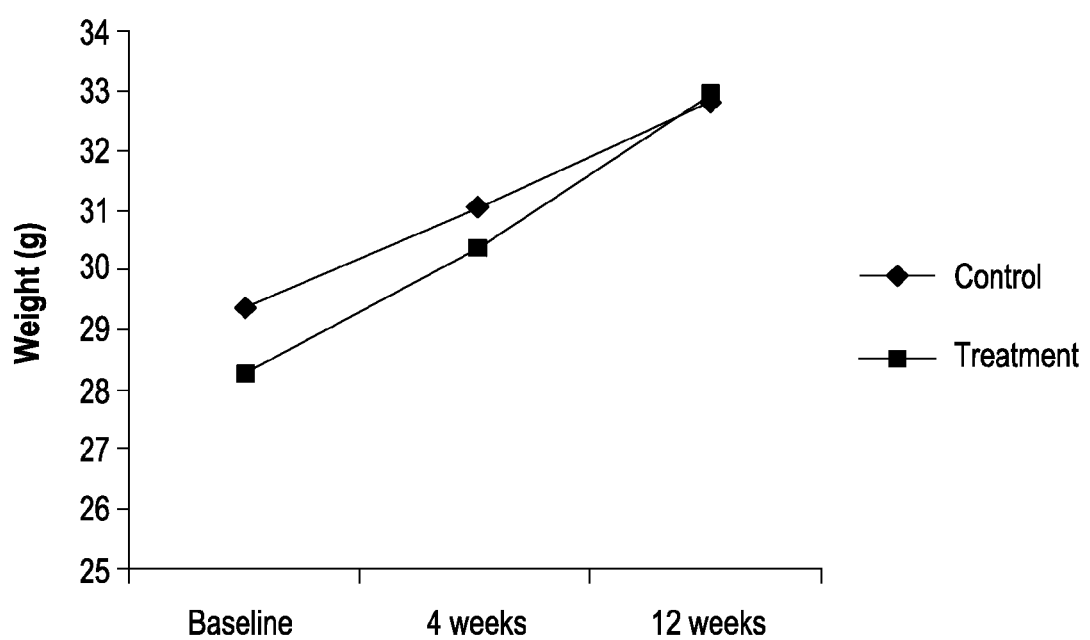
FIG. 1 is a graph of the body weight (g) of the control and treatment groups as a function of time after starting the respective diets.

The present invention is based on the discovery that the build-up of atherosclerotic plaques is caused by the binding of a free fatty acid anion coupled with a divalent or trivalent metal such as calcium, magnesium, or iron in the presence of an alkali solution (greater than pH 7.0) and a triglyceride (fat). The ratio of fatty acid, calcium and fat will determine if the atherosclerotic plaque is a "smear" or waxy (soft plaque) or a hard precipitate (hard plaque). The fatty acid components are predominantly saturated palmitate (C16:0) and stearate (C18:0) fatty acids. These saturated fatty acids have high melting points and together with the calcium salts form hard plaques.

It is believed that reversal of atherosclerotic plaques can be achieved by regular and systematic administration of a composition containing as the active principle MUFAs that have both a very low melting point and a high iodine value (greater than 50 and less than 130). A correlative effect has been observed for fatty acids having a high melting point (i.e. 38° C. or greater) and its atherogenicity. For instance, saturated fatty acids, such as palmitic (C16:0) and stearic (C18:0) fatty acids are considered atherogenic. These saturated fatty acids are solids at both room (about 25° C.) and physiological (about 37° C.) temperatures. In contrast, fatty acids such as palmitoleic acid (C16:1), oleic acid (C18:1) and linoleic acid (C18:2) generally having the same length acyl chains as palmitic and stearic acids, but with one or more unsaturated bonds have low melting point temperatures and therefore are liquids at such temperatures. TABLE 1 provides the melting point of some common fatty acids.

TABLE 1

| Fatty Acid Structure | Fatty Acid Name | Melting Point (° C.) |
| --- | --- | --- |
| C20:5 | Eicosapentaenoic | −54.0 |
| C22:6 | Docosahexaenoic | −50.0 |
| C4:0 | Butyric | −8.0 |
| C18:2 | Linoleic | −5.0 |
| C18:3 | Linolenic | −5.0 |
| C14:1 | Myristoleic | −4.5 |
| C6:0 | Caproic | −3.4 |
| C16:1 | Palmitoleic | −0.5 |
| C18:1 | Oleic | 13.4 |
| C8:0 | Caprylic | 16.7 |
| C20:1 | Eicosenoic | 23.5 |
| C22:1 | Docosenoic | 30.0 |
| C10:0 | Capric | 31.6 |
| C24:1 | Tetracesenoic | 42.5 |
| C12:0 | Lauric | 44.2 |
| C14:0 | Myristic | 53.9 |
| C16:0 | Palmitic | 63.1 |
| C18:0 | Steric | 69.8 |
| C20:0 | Arachidic | 75.3 |
| C22:0 | Behenic | 79.9 |
| C24:0 | Lignoceric | 84.2 |

Many of the fatty acids found in TABLE 1 can be found as triglycerides in natural sources such as plants, nuts and animals. These natural triglyceride sources, however, contain mixtures of many fatty acids differing in both acyl chain length and degree of saturation. For instance, lard (from pigs), tallow (from cattle) and mutton tallow (from sheep) are solid fats at room temperature, and between 40% and 50% of their acyl groups are saturated C16:0 and C18:0. The monounsaturated oleic acid (C18:1) constitutes about 40% to 50% of their acyl content and much of the remainder is polyunsaturated linoleic acid (C18:2). By contrast, most vegetable oils, which are liquids at room temperature, have only 10% to 20% of palmitic and stearic acid esters, with the remainder being mostly unsaturated oleic and linoleic acid esters.

Iodine value is a measure of the degree of carbon-carbon double bonds of an oil or fat. Saturated (having no carbon-carbon double bonds) oils and fats take up no iodine and therefore their iodine value is zero. In contrast, unsaturated oils and fats take up iodine. The more double bonds present, the more iodine is attached, the higher the iodine value, and the more reactive and unstable the oil or fat becomes. It has been discovered that fatty acids with iodine value above 130, can cross-link and polymerize to form deposits within the body while those fatty acids having an iodine value of about 50 to about 130 are more stable and less prone to polymerization and attachment to the arterial walls.

TABLE 2 provides iodine values for some common fatty acids.

TABLE 2

| Fatty Acid Structure | Fatty Acid Name | Iodine Value |
|---|---|---|
| C4:0 | Butyric | 0 |
| C6:0 | Caproic | 0 |
| C8:0 | Caprylic | 0 |
| C10:0 | Capric | 0 |
| C12:0 | Lauric | 0 |
| C14:0 | Myristic | 0 |
| C16:0 | Palmitic | 0 |
| C18:0 | Steric | 0 |
| C20:0 | Arachidic | 0 |
| C22:0 | Behenic | 0 |
| C24:0 | Lignoceric | 0 |
| C24:1 | Tetracesenoic | 69 |
| C22:1 | Docosenoic | 74 |
| C20:1 | Eicosenoic | 81 |
| C18:1 | Oleic | 89 |
| C16:1 | Palmitoleic | 99 |
| C14:1 | Myristoleic | 112 |
| C12:1 | Lauroleic | 128 |
| C18:2 | Linoleic | 181 |
| C18:3 | Linolenic | 273 |

Administration of high concentrations comprising mixtures or blends of greater than about 80% by weight of MUFAs as dietary supplement, nutraceuticals and pharmaceuticals having low melting points and high iodine values can be effective in treating atherosclerosis. Specifically, the present invention provides that high concentrations of MUFAs having melting points of about 29° C. to about 34° C. and iodine values of about 50 to about 130 have an anti-atherogenic effect. Representative examples of such MUFAs are C22:1, C20:1, C18:1, C16:1, C14:1 and C12:1.

The invention herein further provides that administration of high MUFA concentrations of compositions comprising at least two fatty acid groups having a melting point of about 29° C. to about 34° C. and an iodine value of about 50 to about 130 wherein the first fatty acid group has an acyl carbon length chain of 16 carbons or less ("short carbon chain group") and the second fatty acid group has an acyl carbon length chain of 18 carbons or more ("long carbon chain group") and the total weight of the first and second fatty acid group is greater than 80% by weight of the composition is useful for treating atherosclerosis.

The MUFA compositions described herein comprises a first fatty acid group of short carbon chains with at least one member selected from the group of C12:1, C14:1, and C16:1 and a second fatty acid group of long carbon chains with at least one member selected from the group of C22:1, C20:1, and C18:1.

Preferred MUFA compositions are provided that comprises about 18% to about 40% by weight of the first short carbon chain group and about 40% to about 80% by weight of the second long carbon chain group. Representative examples of the compositions contemplated herein with the ratio concentrations of short carbon chain to the long carbon chain MUFAs are provided in TABLE 3.

TABLE 3

| Short Carbon Chain MUFA | Long Carbon Chain MUFA |
|---|---|
| 18%-40% | 60%-80% |
| 20%-40% | 60%-80% |
| 18%-23% | 60%-80% |
| 20%-23% | 60%-80% |
| 20%-40% | 40%-80% |

Methods for treating atherosclerosis are also provided by administering the compositions set forth herein. Examples of such methods include administering the compositions described in TABLE 3 to a patient at about 15 grams per 40 kg of body weight per day for at least 8 weeks.

MUFAs have a single vinylic or carbon-carbon double bound along the acyl hydrocarbon chain. Hereinafter the structure of the fatty acids will be characterized by notations such as Cx:yn-a. The "Cx" indicates that the fatty acyl group contains "x" carbon atoms. The "y" designates the number of carbon-carbon double bonds in the acyl chain and "n-a" designates that the most distal double bond terminates on the "a" the carbon counting from the terminal methyl end.

The MUFAs selected for the present invention include blends or mixtures of fatty acids having low melting point temperature of about 29° C. to about 34° C. and high iodine values of about 50 to about 130. Treatment using a composition combining high concentrations of at least two groups of the selected MUFA wherein at least one member of the first MUFA group is selected from the short carbon chain MUFA (acyl carbon length of 16 carbons or less) and at least one member of the second group of MUFA is selected from the long carbon chain MUFA (acyl carbon length of 18 carbons or greater) are useful for reducing the size and number of plaques in arteries. Non-limiting examples of MUFAs contemplated herein can be found in TABLE 4 below. Representative short carbon chain MUFAs include C12:1, C14:1 and C16:1 and long carbon chain MUFAs include C22:1, C20:1 and C18:1. The MUFAs discussed in the present invention may exist in both the cis or trans configuration and both geometric isomers are contemplated in the present invention.

TABLE 4

| Monounsaturated Fatty Acid | |
|---|---|
| Structure | Name |
| C12:1 | Lauroleic |
| C14:1 | Myristoleic |
| C16:1 | Palmitoleic |
| C18:1 | Oleic |
| C20:1 | Eicosenoic |
| C22:1 | Docosenoic |

The short carbon chain MUFAs and the long carbon chain MUFAs described herein should comprise at least about 80% by weight of the total composition. Preferably the short carbon chain MUFA group comprises about 18% to about 40% by weight of the composition, more preferably about 18% to about 23% and even more preferably about 20% to about 23% of the composition. The long carbon chain MUFA group preferably comprises about 40% to about 80% and more preferably about 60% to about 80% by weight of the composition.

Preferred fatty acids are C16:1 and C18:1. The fatty acid C16:1 can comprise any one of its positional isomers including C16:ln-7, C16:ln-6, C16:ln-5, C16:ln-4, and C16: ln-3 as well as its cis and trans-geometric isomers. A more preferred fatty acid is C16:ln 7. The trivial name for C16:ln 7 is palmitoleic acid which is represented generically by Formula I.

$$CH_3(CH_2)_5CH=CH(CH_2)_7COOH \qquad \text{(Formula I)}$$

C16:1 is generally available in naturally occurring oils ("source oils") although in small amounts. Desired oil fractions containing C16:1 can be readily obtained from various types of oil (i.e., various source oils) such as vegetable oils, seed or nut oils, fish oils, animal fats, or aquatic plants oil, such as salt water or fresh water plants, and certain microbes by conventional cooling and distillation techniques, and/or solvent extraction ("refining" techniques) well known to those skilled in the art. Generally vegetable oils as well as nut or seed oils are not high in the desired content of C16:1. Oil sources that have high amounts of the C16:1 of the present invention include fish oils such as sardine and menhaden that can contain from about 10% to about 16% by weight of C16:ln-7 whereas sperm whale oil can contain about 13% or more by weight. Although nut oils generally do not have C16:ln-7 fatty acids, an exception is macadamia nut oil that contains C16:ln-7 in amounts of from about 16% to about 25% by total weight of the oil but it also contains other undesirable fatty acids. Animal fats such as butter oil, chicken fat, lard, and beef tallow generally have high contents of C16:ln-7 but they also contain high levels of other undesirable fatty acids.

The C16:ln-7 fatty acid as well as the corresponding alcohols, diglycerides, triglycerides and salts can be extracted from the above-noted types of oil (i.e., the source oils) by initially cooling the oil to a temperature below the solidification or melting point temperature of the desired CI6:ln-7 and then removing the remaining liquid portion. The removed liquid oil can then be subjected to distillation wherein compounds having higher boiling points than the C16:ln-7, etc., C14:ln-5, etc., C12:ln-3, can be removed. As should be apparent to one skilled in the art, the cooling-distillation process can be repeated until the C16:1 or its corresponding alcohol, diglyceride, triglyceride and/or salt is obtained in concentrated amounts. Alternatively various one or more solvents can be utilized that dissolve C16:1 (and/or corresponding alcohols, diglycerides, triglycerides and salts) but no other components of the oil so that upon vaporization of the solvent, the selective fatty acid (and/or corresponding alcohols, diglycerides, triglycerides and salts) is obtained. Such techniques and processes are well known to the art and to the literature. For example, see the description as set forth in U.S. Pat. No. 5,198,250, such as in Example 1 thereof hereby fully incorporated by reference.

By refining the source oil, high or concentrated amounts of C16:1 can be obtained such as from about 10% to about 35% or about 50% or about 75% or about 90%. Such refined source oils may also contain low amounts of various saturated fatty acid components such as C 12:0, C 14:0, C16:0, and C18:0, e.g., <20 vol. %, <15 vol. %, ≤12 vol. %, <10 vol. %, and even ≤5 vol. %, based on the total amount of fatty acid components in the composition. Similarly, the refined source oils also contain low amounts of polyunsaturated fatty acid oil components such as C12:2 or C12:3, C14:2 or C14:3, C16:2 or C16:3, C18:2 or C18:3, and the like, e.g., <20 vol. %, <15 vol. %, <12 vol. %, <10 vol. %, and even <5 vol. %, based on the total amount of fatty acid components in the composition.

Various strains of algae are suitable with regard to producing the desired source oil for C16:1. The algae can be grown in tanks containing nutrients therein such as phosphates. Numerous strains of algae have relatively high contents of palmitoleic acid such as cyanobacteria, *Phormidium* sp. NKBG 041105 and *Oscillatoria* sp. NKBG 091600, that have high cis-palmitoleic acid content (54.5% and 54.4% of total fatty acid, respectively). *Phormidium* sp. NKBG 041105 has the highest cis-palmitoleic acid content per biomass (46.3 mg (g dry cell weight)–1), and the cis-palmitoleic acid composition was found to be constant with varying temperature. In a similar manner, other aquatic plants such as sea buckthorn can also be grown and utilized. The algae, sea buckthorn, etc., can then be processed by known techniques such as cooling-distillation or solvent extraction to obtain moderate to high concentrations of C16:ln-7 oil fractions. In addition, WO 2009/105620 published Aug. 29, 2009 and WO 2008/036654 published Mar. 27, 2008 identifies additional algae suitable as source oil for C16:1. Both publications are hereby fully incorporated by reference.

The fatty acid C18:1 can comprise any of its positional isomers including C18:ln 9. Fatty acid C18:ln 9 known by its trivial name as oleic acid is a preferred fatty acid of C18:1 and is represented generically by Formula II.

$$CH_3(CH_2)_7CH=CH(CH_2)_7COOH \qquad \text{(Formula II)}$$

C18:1 can be extracted from natural sources such as safflower oil or olive oil as described in U.S. Pat. No. 6,664,405 or purchased from commercial sources such as Sea Land Chemical, Cargill, and Emory.

The MUFAs contemplated herein may be used in any form including as a free fatty acid, fatty acid ethyl ester, fatty acid amide or derivatives thereof, salt, monoglyceride, diglyceride, or triglyceride. Any modifications to the MUFAs should result in a physiologically acceptable composition. As used herein, the term "physiologically acceptable" ester or salt means an ester or salt form of the active ingredient that is compatible with the other ingredients of a dietary supplement, nutraceutical or pharmaceutical composition which is not deleterious to the subject receiving the composition.

As used herein, the term "monoglyceride" refers to a fatty acid covalently bonded to a glycerol molecule through an ester linkage. The term "diglyceride" refers to two fatty acid chains, covalently bonded to a glycerol molecule through an ester linkages. The term "triglyceride" refers to three fatty acid chain covalently bonded to a glycerol molecule through ester linkages. Each of the fatty acid chains bound to the glycerol molecule of the di or triglyceride, may or may not be identical.

The monounsaturated fatty alcohols can be derived from the above MUFAs by reduction thereof as known to the literature and to the art as by a strong base such as lithium aluminum hydride and secondary separation steps such as, but not limited to, fractional distillation. The fatty alcohol derivative will thus have the same number of total carbon atoms therein, will be monounsaturated, and will contain the double bond at the same location as set forth with regard to the MUFAs discussed herein. Suitable salts of the above MUFAs, or the monounsaturated fatty alcohols, or the monounsaturated fatty acid, mono, di- or triglyceride include the various halides such as chlorine.

It has been discovered that atherosclerosis can be treated by administration of compositions containing as the active principal greater than 80% by weight of MUFAs having melting points of about 29° C. to about 34° C. and iodine values of about 50 to about 130 and preferably about 68 to about 130. The MUFA compositions provided herein comprises a first group of short carbon chain MUFAs and a second group of long carbon chain MUFAs. A preferred MUFA from the short carbon chain group is C16:1 and preferred MUFA from the long carbon chain group is C18:1. Compositions comprising blends or mixtures of such MUFAs include about 18% to about 40% by weight of C16:1 and about 40% to about 80% by weight of C18:1. Preferably such concentrations include about 18% to about 23% by weight of C16:1 and about 60% to about 80% by weight of C18:1. More preferably about 20% to about 23% by weight of C16:1 and about 60% to about 80% by weight of C18:1. The regular and systematic administration of said composition has shown to inhibit atherosclerotic plaque formation and reduce the size and number of plaques in arteries.

"Treat," "Treatment," or "Treating" refer to both therapeutic treatment and prophylactic or preventative measures, wherein the object is to reduce, inhibit, prevent or slow down (lessen) an undesired physiological change or disorder, such as the development or progression of atherosclerotic plaque.

Reducing atherosclerotic plaques includes both preventing the formation of new atherosclerotic plaques and/or reducing the size of existing atherosclerotic plaques. Reducing plaque size can include reducing (i) the percentage of the surface area affected by atherosclerotic plaque in one or more arteries of a mammal, (ii) the number of plaques found in one or more arteries of a mammal, and/or (iii) the severity of such plaques. For example, the reduction can comprise a 5%, 10%, 20%, 30%, 40%, 50%, 60%, 70%, 80%, 90%, or 100% reduction, or any point in between, compared to an untreated or control subject as determined by any suitable measurement technique or assay disclosed herein or known in the art. Atherosclerotic plaque reduction may occur in specific arteries such as aortic arteries, coronary arteries, carotid arteries, and cerebral arteries.

The term "composition" as used herein includes therapeutic and dietary formulations. The compositions of the present invention are formulated in the sense that the fatty acid content of the dietary supplement, nutraceutical or pharmaceutical composition is manipulated or adjusted to provide the desired high concentrations of MUFAs having low melting points and iodine values of about 50 to about 130, represented by the short and long carbon chain MUFA; C22:1, C20:1, C18:1, C16:1, C14:1 and C12:1. The term "dietary supplement" is a product intended for ingestion that contains a nutrient. The nutrient may be one, or any combination, of the following substances: vitamins, minerals, fiber, fatty acids, or amino acids, among other substances. The term "nutraceutical" is any foodstuff that has physiological activity beyond that of the foodstuff. The high MUFA compositions contemplated herein are not commonly found in foodstuff.

The MUFA provided herein is formulated, meaning that the individual components are mixed together from purified sources, to form the high concentrations of short and long carbon chain MUFAs described herein. Alternatively, naturally occurring foodstuffs can be enhanced into the high composition of MUFAs described herein. Such enhanced foodstuffs may have low levels of MUFAs present in the foodstuff. The long and short carbon chain MUFAs provided herein are then added or supplemented to the foodstuffs such that the final short and long carbon chain MUFA concentration in the foodstuff is greater than about 80% by weight total and the percentage weight of each group of short and long carbon chain MUFA falls within the concentration ranges provided in TABLE 3.

The composition contemplated herein may also be administered to a mammal in the form of a pharmaceutical composition. Such a pharmaceutical composition may contain only the MUFAs contemplated herein as the active ingredients. The pharmaceutical composition may also contain said active ingredients together with one or more pharmaceutically acceptable carriers and any additional ingredients.

A "pharmaceutically acceptable carrier" is meant to encompass any carrier, which does not interfere with effectiveness of the activity of the active ingredient and is not toxic to the host to which it is administered. Pharmaceutically acceptable carriers are known to those of ordinary skill in the art.

"Additional ingredients" means one or more of the following: excipients, surface active agents, dispersing agents, inert diluents, granulating agents, disintegrating agents, binding agents, lubricating agents, sweetening agents, flavoring agents, coloring agents, preservatives, physiologically degradable compositions (e.g., gelatin), aqueous vehicles, aqueous solvents, oily vehicles and oily solvents, suspending agents, dispersing agents, wetting agents, emulsifying agents, demulcents, buffers, salts, thickening agents, fillers, emulsifying agents, antioxidants, antibiotics, antifungal agents, stabilizing agents, and pharmaceutically acceptable polymeric or hydrophobic materials. Other "additional ingredients" which may be included in the pharmaceutical compositions are known. Suitable additional ingredients are described in *Remington's Pharmaceutical Sciences*, Mack Publishing Co., Genaro, ed., Easton, Pa. (1985).

Pharmaceutical compositions described herein may be prepared by any known method or method developed hereafter in the art of pharmacology. In general, such preparatory methods include the step of combining said active ingredients with a carrier and/or one or more other accessory ingredients, and then, if necessary or desirable, shaping or packaging the product into a desired single- or multi-dose unit.

Although the pharmaceutical compositions provided herein are principally directed to those suitable for ethical administration to humans, it is understood that such compositions are generally suitable for mammals of all sorts.

Oral formulations may be prepared, packaged, and/or sold as a discrete solid dose unit such as a tablet, a hard or soft capsule, a cachet, a troche, or a lozenge, each containing a predetermined amount of the active ingredient. Other oral formulations include powdered or granular formulations, aqueous or oily suspensions, aqueous or oily solutions, and emulsions. As used herein, an "oily" liquid is a carbon-containing liquid molecule that exhibits a less polar character than water. Hard capsules and soft gelatin capsules containing an active ingredient may be manufactured using a physiologically degradable composition, such as gelatin. Hard capsules may further include inert solid diluents such as calcium carbonate, calcium phosphate, and kaolin. While calcium diluents are acceptable, its concentration should be minimized to avoid negative interactions with the fatty acids. Soft gelatin capsules containing the MUFAs contemplated herein as the active ingredients may be manufactured using a physiologically degradable composition, such as gelatin. Such soft capsules contain the active ingredient, which may be mixed with other excipients. Liquid pharmaceutical formulations that are suitable for oral administration may be prepared, packaged and sold in liquid form.

Any of the MUFAs, dietary supplement, nutraceuticals, and pharmaceutical compositions described herein may be administered according to the methods described herein. Generally, the compositions described herein may be administered at about 15 grams per 40 kg of body weight. The dosage amount may vary according to other factors such as the person's age, health, and/or severity of existing atherosclerotic plaques.

By way of non-limiting examples, the compositions described herein may be administered to a person at about 15 grams to about 60 grams per day or any value in between. A person weighing over 72 kg, can be administered doses ranging at about 30 grams to about 60 grams total per day. Preferably about 30 grams, about 40 grams, about 50 grams and about 60 grams total per day or any value in between. Persons weighing less than 72 kg may be administered doses of about 15 grams to about 30 grams total per day or any value in between. Preferably about 15 grams, about 20 grams, about 25 grams and about 30 grams or any value in between.

A person may receive the high concentrations of the MUFAs compositions contemplated herein as a dietary supplement, nutraceutical, or pharmaceutical in any form described herein including liquid, solid or semi-solid. The person may undergo treatment with said high concentrations of the MUFAs compositions before or after an atherosclerotic plaque is detected. It may be advantageous to administer the MUFAs compositions to persons having high risk factors for developing atherosclerotic plaques. The methods contemplated herein may be administered daily and continue for about eight weeks or until the atherosclerotic plaques disappear or even longer.

The MUFAs composition for treating atherosclerosis comprises a combination, mixture or blend of a high concentration of MUFAs having melting point temperatures of about 29° C. to about 34° C. and iodine values of about 50 to about 130. The said high concentration of MUFAs may contribute to at least about 80% to about 100% by weight of the total composition. The said MUFAs may further contribute to at least about 90% and 95% by weight of the total composition. Optionally, other fatty acids may be incorporated into the said high MUFAs composition. Such optional fatty acids may be saturated and polyunsaturated fatty acids. It is preferred that such optional fatty acids comprise no more than 15% of the total weight of the composition.

Preferred fatty acids from the short carbon chain group include C16:1 and from the long carbon chain group include C18:1. The compositions described herein are not limited to a single fatty acid selected from each group. For example, C16:1 is selected as a representative MUFA, however, it may be combined with other short carbon chain members of the group including C12:1 or C14:1 such that the entire composition of the short chain MUFA members may not exceed 40% by weight of the composition. Likewise, the long carbon chain members of the MUFA discussed herein are not limited to C18:1 as it may be comprised of other members including C22:1 and C20:1 such that the entire composition of the long carbon chain members do not exceed about 80%. The combination of short carbon chain and long carbon chain MUFAs may comprise at least about 80% to about 100% by weight of the total composition. The combined short carbon chain and long carbon chain MUFAs may further comprise at least about 90% and 95% by weight of the total composition.

Optionally, other fatty acids including saturated and polyunsaturated fatty acids may be incorporated into the C16:1 and C18:1 fatty acid composition. Such optional saturated fatty acid and polyunsaturated fatty acids may not exceed more than about 15% by weight of the entire composition. The saturated fatty acids may comprise a single or multiple members of saturated fatty acids and may further comprise any value up to about 15% by weight of the total composition, preferably up to about 7% by weight, and more preferably about 1% to about 5% by weight of the total composition. Non-limiting examples of saturated fatty acids include C16:0, C12:0, C14:0, and C10:0. TABLE 5 provides common saturated fatty acids contemplated in the present invention.

TABLE 5

| Saturated Fatty Acid | |
|---|---|
| Structure | Name |
| C4:0 | Butyric |
| C6:0 | Caproic |
| C8:0 | Caprylic |
| C10:0 | Capric |
| C12:0 | Lauric |
| C14:0 | Myristic |
| C16:0 | Palmitic |
| C18:0 | Steric |
| C20:0 | Arachidic |
| C22:0 | Behenic |
| C24:0 | Lignoceric |

The polyunsaturated fatty acids may comprises a single or multiple members of polyunsaturated fatty acids and may further comprise any value up to about 15% by weight of the total composition, preferably up to about 7% by weight, and more preferably about 1% to about 5% by weight of the total composition. Non-limiting examples of polyunsaturated fatty acids include C18:2, C18:1 and C20:4. TABLE 6 provides common polyunsaturated fatty acids contemplated in the present invention.

TABLE 6

| Polyunsaturated Fatty Acids | |
|---|---|
| Structure | Name |
| C16:2 | Hexadecadienoic |
| C16:4 | Hexadecatetradienoic |
| C18:2 | Linoleic |
| C18:3 | Linolenic |
| C20:4 | Arachidonic |
| C20:5 | Eicosapentaenoic |
| C21:5 | Heneicosanoic |
| C22:2 | Docosadienoic |
| C22:3 | Docosatrienoic |
| C22:4 | Docosatetraenoic |
| C22:6 | Docosahexaenoic |

Optionally, the composition may comprise trace or minute amounts of other fatty acids. The trace fatty acids will be understood to refer to any fatty acids found commonly in the mammal's diet ranging from C8:0 to C20:4 including those fatty acids described herein. Such trace amounts of fatty acids may optionally be present at up to about 3% by weight of the total composition.

The MUFA discussed herein including C16:1 and C18:1 is typically formulated, meaning that the individual components are first refined and purified from its source material, then mixed together to form the desired composition described herein. It is further contemplated that naturally occurring foodstuffs can be enhanced into the composition described herein by adding, adjusting or substituting the foodstuff with at least one of the MUFA described herein such that the desired percentage weight of the C16:1 and C18:1 is reached. Other fatty acids including saturated fatty acids, and polyunsaturated fatty acids may optionally be present in said enhanced composition, however, preferably such optional fatty acids may not exceed about 15% by weight of the overall composition.

Representative compositions encompassed by the present invention and within the scope of the invention are provided in the following examples. These examples and preparations which follow are provided to enable those skilled in the art to more clearly understand and to practice the present invention. They should not be considered as limiting the scope of the invention, but merely as being illustrative and representative thereof.

| Composition I | |
|---|---|
| 18-23% | C16:1 |
| 60-80% | C18:1 |
| 0-5% | saturated fatty acid |
| 0-5% | polyunsaturated fatty acid |
| 0-3%. | trace fatty acids |

| Composition II | |
|---|---|
| 18-23% | C16:1 |
| 60-80% | C18:1 |
| 2-5% | C16:0 |
| 2-5% | C18:2 |
| 1-3%. | trace fatty acids |

| Composition III | |
|---|---|
| 20% | C16:1n7 |
| 60%-80% | C18:1 |
| 2%-5% | C16:0 |
| 2%-5% | C18:2 |
| 1%-3% | trace fatty acids |

| Composition IV | |
|---|---|
| 20%-40% | C16:1 |
| 40%-60% | C18:1 |
| 0-5% | saturated fatty acid |
| 0-5% | polyunsaturated fatty acid |
| 0-3% | trace fatty acids |

| Composition V | |
|---|---|
| 20%-23% | C16:1 |
| 60%-80% | C18:1 |
| 1%-5% | saturated fatty acid |
| 1%-5% | polyunsaturated fatty acid |

| Composition VI | |
|---|---|
| 20%-40% | C16:1 |
| 40%-60% | C18:1 |
| 0%-5% | saturated fatty acid |
| 0%-5% | polyunsaturated fatty acid |

| Composition VII | |
|---|---|
| 20%-40% | C16:1, C14:1 and C12:1 |
| 40%-80% | C22:1, C20:1, and C18:1 |
| Up to 15% | saturated fatty acid and polyunsaturated fatty acid |

| Composition VIII | |
|---|---|
| 20% | C16:1n7 |
| 60% | C18:1 |
| 15% | C16:0 |
| 5% | C18:2 |

Example 1

Animal feeding experiments were performed on thirty-four male Apo E knockout mice. The mice were fed normal mouse chow until 2 months of age and then randomly allocated into two groups (n=17 each). One group of mice was fed a control Western high-fat diet (Control Diet) containing saturated fat and C18:1 in semi-solid form. The other group was fed a high concentration of C16:1 and C18:1 fatty acid diet (Treatment Diet) in liquid form. The consistency of the food was mixed into a paste and water was freely available. Blood samples were obtained 8 and 12 weeks after initiation of the diet. At 12 weeks, all mice were sacrificed and results analyzed.

| Diet Composition | |
|---|---|
| Control Diet | Treatment Diet |
| F5722 | F5723 |
| 20% Saturated Fat | 20% C16:1n-7 |
| 60-80% C18:1 | 60-80% C18:1 |
| 2-5% C16:0 | 2-5% C16:0 |
| 2-5% C18:2 | 2-5% C18:2 |
| 1-3% trace fatty acids | 1-3% trace fatty acids |
| Cholesterol 2.1 gm/kg (Bio-Service, Frenchtown, NJ) | Cholesterol 2.1 gm/kg (Bio-Service, Frenchtown, NJ) |

The 20% saturated fat in the Control Diet contains over 90% by weight total of saturated fatty acids comprising: caprylic, decanoic, lauric, myristic and palmitic saturated fatty acids and about 10% by weight total of monounsaturated oleic acid and other fatty acids.

Quantification of Aorta Lesions

The surface area of aorta occupied by atherosclerotic lesions was quantified by en face oil red O staining, using an approach modified from Palinski et al, "Increased autoantibody titers against epitopes of oxidized LDL in LDL receptor-deficient mice with increased atherosclerosis," Arterioscler Thromb Vas Biol. 1995; 15(10):1569-76. After mice were killed, a catheter was inserted into the left ventricle and the arterial tree was perfused with PBS (25 ml), followed by 4% buffered formaldehyde (20 ml, PH 7.4) at a pressure of 100 mm Hg. Under a microscope (Leica M500) the entire aorta attached to the heart was dissected and the adventitial fat was dissected. The ascending aorta was transected, and the heart was placed in histo-choice for assessment of aortic root atherosclerosis. The remainder of the aorta was stained with Sudan IV. The aorta was opened longitudinally, pinned en face on a black silicone-covered dish, and photographed while immersed in PBS. The lesion area was quantified as the percent surface area occupied by Sudan IV red-staining using a computerized digital microscopic planimetry software package (Image-pro Plus, Version 4.0 for Windows, media Cybernetics, Silver Spring, Md.).

Quantification of Aortic Sinus Lesions

After fixation in histo-choice, the hearts were placed in optimum cutting temperature (OCT) compound, and frozen on dry ice. Cryostat sections (10 μm), starting at the apex and progressing through the aortic valve area into the ascending aorta, were cut at the level of the aortic sinus, collected on superfrost microscopic glass slides, and stored at −20° C. until analyzed. Sections were stained with oil red O and hematoxylin (Sigma) and counterstained with light green (Sigma). With the aortic sinus, lesions from 5 sections, each 80 μm apart were measured, using a computerized digital microscopic planimetry software package (Image-pro Plus, Version 4.0 for Windows, media Cybernetics, Silver Spring, Md.)

Assays for Serum Lipids

Serum samples, collected at time of the beginning and the 2 month time point were obtained by tail vein, and euthanasia at 3 months of age by cardiac puncture, were individually evaluated for blood lipids. Enzymatic in vitro tests for the direct quantitative determination of triglycerides, cholesterol and HDL-cholesterol on Roche automated clinical chemistry analyzers were used. All reagents were from Roche Diagnostics (Indianapolis Ind.) and the instrument is a Hitachi 911. The assays all used colorimetric methods with calibrated standards also from Roche, which are NIST (the National Institute of Standards) traceable. The results of the assays were further verified using the CDC (the Center for Disease Control) lipid standardization program.

Statistical Analysis

Data are presented as mean±SD. Statistical analysis was performed with t-test. $P<0.05$ indicates statistical significance.

Results Body Weight

No significant difference in body weight was observed at the baseline, 4 weeks and 12 weeks follow-up between the control and treatment groups ($P>0.05$, FIG. 1). FIG. 1 is a chart representing the body weight (g) of the control and treatment groups as a function of time after starting the respective diets. There was no significant difference at the baseline and follow-up time points.

Blood Lipid Level

TABLE 7 shows the resulting serum concentrations of blood lipids. Levels of total cholesterol and total triglycerides were not significant differences between the two groups at both 8 weeks and 12 weeks follow-up. HDL-cholesterol in the experimental treatment group was significantly increased compared to the baseline and the control group at 8 and 12 weeks follow-up ($P<0.01$)

TABLE 7

|  | Chol (mg/dL) | Trig (mg/dL) | HDL (mg/dL) |
| --- | --- | --- | --- |
| Baseline |  |  |  |
| Control | 248.2 ± 63.1 | 108.1 ± 60.0 | 22.2 ± 6.8 |
| Treatment | 254.1 ± 58.2 | 107.1 ± 24.4 | 20.7 ± 6.9 |
| 8 Week Follow-up |  |  |  |
| Control | 1021.3 ± 231.3 | 132.9 ± 51.3 | 25.3 ± 4.4 |
| Treatment | 960.4 ± 178.1 | 135.4 ± 39.3 | 40.3 ± 6.9* |
| 12 Week Follow-up |  |  |  |
| Control | 944.3 ± 238.3 | 112.7 ± 44.0 | 20.4 ± 6.5 |
| Treatment | 891.8 ± 181.5 | 100.1 ± 47.0 | 36.2 ± 9.8* |

*Compared to the control *P < 0.01

TABLE 7 summarizes the levels of blood lipids at baseline, 8 weeks and 12 weeks follow-up for animals that received control Western diet and treatment diet.

Atherosclerotic Lesion Formation

Figure 2:
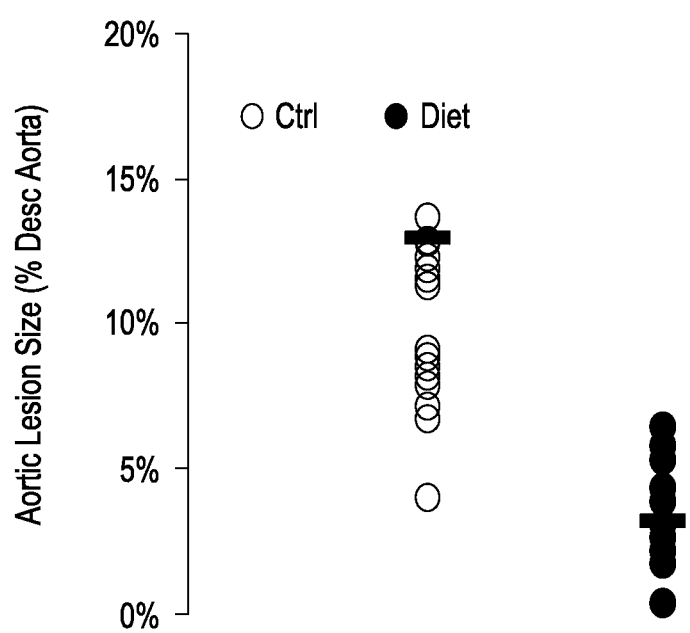
FIG. 2 is a graph showing the lesion area 3 months after diet in the descending thoracic aorta from animals fed a control versus treatment diet.

Oil red O staining of aortic root displayed severe atherosclerosis of the aortic sinus in the control group (FIG. 2, TABLE 8). The treatment group revealed significant reductions in the size of atherosclerotic lesion by 47% relative to the control group (the control 0.33±0.09 vs the treatment 0.18±0.07 mm² P<0.00). Atherosclerotic lesion area in the aorta of the experimental treatment group was also significantly inhibited (TABLE 9) (control 9.63±2.80% vs treatment 3.17±1.60% P<0.001).

TABLE 8

|  | Aortic Sinus Lesion Size (mm²) | |
| --- | --- | --- |
|  | Control | Treatment |
|  | 0.33 ± 0.09 | 0.18 ± 0.07** |
| Pilot, 20 ug IFN plasmid | 0.45 ± 0.11 | 0.32 ± 0.11 |
| Cohort 2, 2 ug IFN plasmid | 0.31 ± 0.08 | 0.31 ± 0.10 |
| Cohort 3, 20 ug IFN Plasmid + Rosuvastatin | 0.36 ± 0.10 | 0.35 ± 0.10 |

TABLE 9

|  | Aortic Lesion (%) | |
| --- | --- | --- |
|  | Control | Treatment |
|  | 9.63 ± 5.9 | 3.17 ± 1.6* |
| Pilot, 20 ug IFN plasmid | 12.12 ± 5.9 | 7.10 ± 2.0* |
| Cohort 2, 2 ug IFN plasmid | 6.72 ± 4.2 | 5.31 ± 1.8 |
| Cohort 3, 20 ug IFN Plasmid + Rosuvastatin | 6.40 ± 3.6 | 7.80 ± 6.3 |
| Rosuvastatin (20 mg/kg/day)(1) | 21.9 ± 2.9 | 11.9 ± 1.9* |
| Isoquercitrin study 1 (2) | 9.5 ± 4.1 | 5.9 ± 2.5* |
| Isoquercitrin study 2 (2) | 8.8 ± 3.5 | 4.4 ± 1.5* |

Compared to the control group, *P < 0.05, **P < 0.001
(1) Enomoto S., et al Rosuvastatin prevents endothelial cell death and reduces atherosclerotic lesion formation in ApoE-deficient mice. Biomed Pharmacother. 2007; xx 1-8.
(2) Motoyama, K., et al, Atheroprotective and plaque-stabilizing effects of enzymatically modified isoquercitrin in atherogenic apoE-deficient mice.

FIG. 2 shows the lesion area 3 months after diet in the descending thoracic aorta from animals fed control Western diet (open circles) and treatment diet (red circles). Solid bars represent the mean lesion size. Representative oil red O staining of the aortic root to detect atheromatous lesions from animal that received control Western diet (A) and from animal that received the treatment diet (B) were performed. The results indicate a dramatic decrease in the degree of atherosclerosis in the aortic root sinus in animals that received the treatment diet.

The treatment group showed significant increase in HDL-cholesterol at 8 and 12 weeks follow-up compared to the control group. This effect may be attributed to the high concentrations of C16:1 and C18:1 in the diet. The data further suggests that administration of high concentrations of C16:1 and C18:1 can significantly inhibit the atherosclerotic formation at the aortic root and dramatically decrease the atherosclerotic area of aorta in atherogenic apoE-deficient mice.

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

All patents, patent applications and publications cited in this application are hereby incorporated by reference in their entirety for all purposes to the same extent as if each individual patent, patent application or publication were so individually denoted.

The invention claimed is:

1. A composition comprising two monounsaturated fatty acids (MUFA) groups having a melting point temperature of about 29° C. to about 34° C. and an iodine value of about 50 to about 130, wherein,
   the first MUFA group comprises MUFA having an acyl carbon length chain of 16 carbons or less;
   the second MUFA group comprises MUFA having an acyl carbon length chain of 18 carbons or more; and
   the total weight of the first and second MUFA group is greater than 80% by weight of the composition.

2. The composition of claim 1, wherein the first MUFA group comprises at least one member selected from the group of C12:1, C14:1 and C16:1 and the second MUFA group comprises at least one member selected from the group of C22:1, C20:1 and C18:1.

3. The composition of claim 1 wherein the first MUFA group is present at about 18% to about 40% by weight of the composition and the second MUFA group is present at about 40% to about 80% by weight of the composition.

4. The composition of claim 1, wherein the MUFA group is present at about 20% to about 40% by weight of the composition and the second MUFA group is present at about 60% to about 80% by weight of the composition.

5. The composition of claim 1 wherein the first MUFA group is present at about 18% to about 23% by weight of the composition and the second MUFA group is present at about 60% to about 80% by weight of the composition.

6. The composition of claim 1 wherein the first MUFA group is present at about 20% to about 23% by weight of the composition and the second MUFA group is present at about 60% to about 80% by weight of the composition.

7. The composition of claim 1 wherein the acyl carbon chain of the MUFA in the first and second groups are selected from at least one member of the group consisting of free fatty acid, alcohol, diglyceride, triglyceride and salt.

8. The composition of claim 1 wherein C16:1 is present in the first MUFA group at about 18% to about 23% by weight of the composition and wherein C18:1 is present in the second MUFA group at about 60% to about 80% by weight of the composition.

9. The composition of claim 8 wherein the C16:1 is selected from at least one member of the group consisting of C16:1n-7, C16:1n-6, C16:1n-5, C16:1n-4 and C16:1n-3.

10. The composition of claim 8, wherein the C16:1 is a cis-isomer.

11. The composition of claim 8, wherein the C16:1 and C18:1 is an acyl carbon chain selected from at least one member of the group consisting of free fatty acid, alcohol diglyceride, triglyceride and salt.

12. The composition of claim 8, wherein the C18:1 is C18:1n-9.

13. The composition of claim 1, wherein the composition further comprises up to about 15% by weight of saturated fatty acid and polyunsaturated fatty acid.

14. The composition of claim 13 wherein the saturated fatty acids is selected from the group consisting of C16:0, C12:0, C14:0 and C10:0.

15. The composition of claim 13, wherein the saturated fatty acid is about 1% to about 5% by weight.

16. The composition of claim 13 wherein the polyunsaturated fatty acid is selected from the group consisting of C18:2, C18:3 and C20:4.

17. The composition of claim 13 wherein the polyunsaturated fatty acid is about 1% to about 5% by weight.

18. The composition of claim 1 further comprising up to about 3% by weight trace fatty acids.

19. The composition of claim 1 wherein the composition is liquid.

20. A composition comprising:
   about 20% to about 40% by weight of C16:1;
   about 40% to about 80% by weight of C18:1;
   up to about 7% of saturated fatty acids; and
   up to about 7% of polyunsaturated fatty acids.

21. The composition of claim 20, comprising
   about 20% to about 23% by weight of C16:1;
   about 60% to about 80% by weight of C18:1;
   about 1 to about 5% of saturated fatty acids; and
   about 1 to about 5% of polyunsaturated fatty acids.

22. A method of treating atherosclerosis in a patient comprising administering the composition of claim 1 in an amount from about 15 grams per about 40 Kg of body weight per day.

23. The method of claim 22 wherein the composition is administered for at least 8 weeks.

* * * * *